United States Patent [19]

Magrath

[11] Patent Number: 4,539,985

[45] Date of Patent: Sep. 10, 1985

[54] ASPIRATOR AND RESUSCITATOR FOR NEWBORN ANIMALS

[76] Inventor: Joseph M. Magrath, P.O. Box 148, McCook, Nebr. 69001

[21] Appl. No.: 500,770

[22] Filed: Jun. 3, 1983

[51] Int. Cl.³ .............. A61M 16/00

[52] U.S. Cl. .............. 128/205.13; 128/205.17; 128/914; 604/133; 417/472; 92/89

[58] Field of Search .............. 128/205.13, 207.14, 128/207.15, 207.16, 205.16, 205.17, 728, 914, 203.28; 604/37, 132, 133, 153, 212; 417/472, 234; 92/89

[56] References Cited

U.S. PATENT DOCUMENTS

| | | | |
|---|---|---|---|
| 513,924 | 1/1894 | Hartnett | 128/205.16 |
| 2,399,643 | 5/1946 | Kreiselman | 128/205.13 |
| 3,875,941 | 4/1975 | Adair | 604/133 |
| 4,241,740 | 12/1980 | Brown | 128/728 |

FOREIGN PATENT DOCUMENTS

| | | | |
|---|---|---|---|
| 1053064 | 1/1954 | France | 417/472 |

*Primary Examiner*—Henry J. Recla

*Attorney, Agent, or Firm*—Wm. Griffith Edwards

[57] ABSTRACT

An aspirator and resuscitator for newborn animals comprising a cylindrical accordion bellows and adaptors for removing fluids from the nasal and oral passages and for delivering air to and removing air from the breathing passages. The bellows and an adaptor are connected to a central handle which is also the fluid conductor between the bellows and the adaptor. The position and arrangement of the handle provide an effective grip for the whole hand and facilitate the holding and operating of the device effectively and quickly and with safety for the animal. An arrangement is provided for assuring effective and uniform stacking or compressing of the bellows pleats and minimizing the likelihood of damage to the bellows during use.

7 Claims, 8 Drawing Figures

ASPIRATOR AND RESUSCITATOR FOR NEWBORN ANIMALS

This invention relates to apparatus for removing liquids or fluid material from the air passages of newborn animals and for supplying air or oxygen to such animals for resuscitation.

BACKGROUND AND PRIOR ART

Various forms of apparatus have been provided heretofore for removing fluid substances from the oral and nasal passages of animals and for supplying air or oxygen for resuscitation. For example, U.S. Pat. No. 3,628,532 Magrath discloses an aspiration and resuscitation apparatus for supplying pressurized oxygen to the trachea of an animal and for utilizing the pressurized gas to produce a low-pressure zone for removing fluids from the air passages of the animal; a detachable tube or face mask is provided for communication with the animal's air passages. Other apparatus used in the medical field has employed accordion or pleated bellows for supplying air to and withdrawing air from the air passages of patients; U.S. Pat. No. 2,399,643 Kreiselman and No. 2,944,546 Ziherl et al. disclose examples of such apparatus.

The newborn young of cows, pigs, and other domestic animals may require aspiration and resuscitation immediately after birth. It is, therefore, desirable to provide readily portable and easily operated apparatus for use wherever such birth may occur. It is also desirable that the aspirator and resuscitator be of simple construction and be easily and effectively usable by one operator. By providing an aparatus which is reliable in operation and can be readily available it becomes possible to save many newborn animals which otherwise would be lost. Accordingly it is an object of my invention to provide an improved portable device for the aspiration and resuscitation of newborn animals.

It is another object of my invention to provide an aspirator and resuscitator for newborn animals which is of simple construction and may be applied quickly to the animal and operated immediately to effect aspiration and resuscitation of the animal in the few minutes available after birth.

It is another object of my invention to provide an improved resuscitator having quick detachable members, one for aspiration and one for resuscitation, whereby a disabled newborn animal may be aspirated and resuscitated in quick succession within the short time interval available after birth.

It is a further object of my invention to provide a readily portable bellows-type aspirator and resuscitator including an improved handle arrangement whereby the operator may hold and grip the device firmly in one hand while operating the bellows by pressing the hands toward one another to discharge air and releasing the other hand to recharge the bellows.

It is a still further object of my invention to provide an improved readily portable resuscitator of the bellows type including means for generating characteristic sounds of air entering and leaving the bellows which may be utilized by the operator for aiding the timing of the inflation and deflation of the bellows.

It is another further object of my invention to provide an improved readily portable bellows-type resuscitator including means for limiting the rate of flow of air returning to the bellows.

SUMMARY OF THE INVENTION

The aspirator and resuscitator of this invention includes a generally cylindrical bellows which is normally in its extended position and an adaptor for providing communication with the air passages of an animal. Two adaptors are provided, a catheter for aspirating the air passages and a face mask for fitting over the oral and nasal openings during resuscitation. Either adaptor is detachably secured to the bellows by a rigid tubular handle which provides a full hand grip for holding the apparatus firmly during operation. This arrangement enables the operator to hold the resuscitator firmly in communication with an animal's air passages while pressing the bellows between his hands to force air into the passages and then releasing the bellows to draw air or other fluid from the passages. When the device is used as an aspirator, the release of the bellows draws mucous or amniotic fluid or the like from the air passages to free them for breathing. The arrangement of the handle between the bellows and the adaptor enables the operator to hold the apparatus firmly to prevent longitudinal movement toward or away from the animal during the operation of the bellows. The ready portability and simplicity of the apparatus together with the full hand grip and ease of compressing and releasing the bellows makes the apparatus admirably suited for the treatment of newborn animals wherever they may be in the barn or in the field.

Further objects and advantages of my invention will become apparent from the following description and the features of novelty which characterize my invention are pointed out with particularity in the claims annexed to and forming a part of this specification.

BRIEF DESCRIPTION OF THE DRAWINGS

For a better understanding of the invention, reference may be had to the accompanying drawings in which.

DESCRIPTION OF THE PREFERRED EMBODIMENTS

Figure 1:
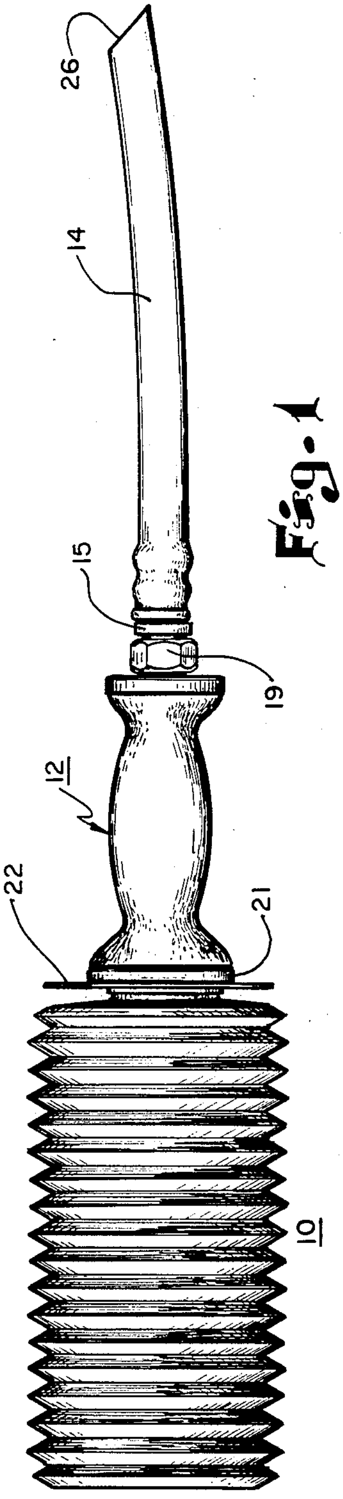
FIG. 1 is an elevation view of one embodiment of my invention for use as an aspirator.
Figure 2:
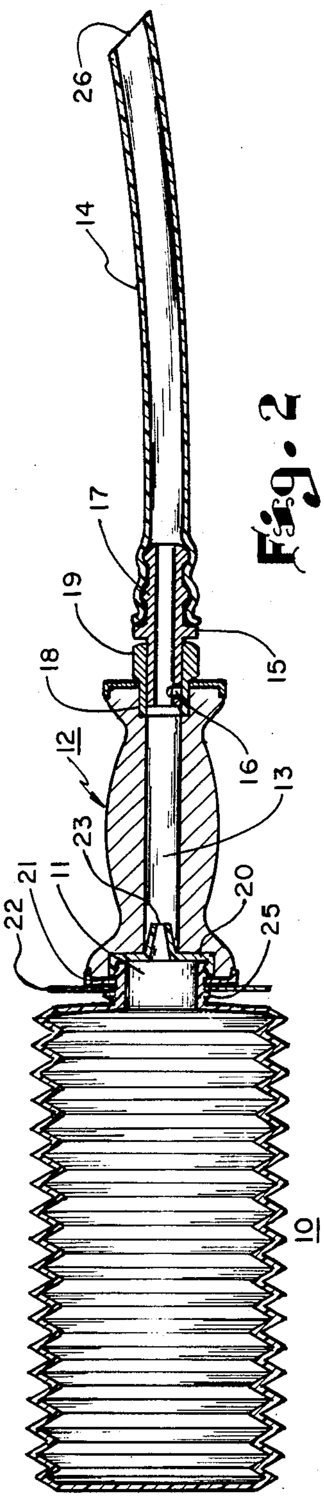
FIG. 2 is a longitudinal sectional view of the device of FIG. 1.

Referring now to the drawings, the aspirator illustrated in FIGS. 1 and 2 comprises an accordion or pleated bellows 10 made of a plastic material which remains flexible at low temperatures; a high-density polyethylene is suitable for this purpose. In FIGS. 1 and 2, the bellows 10 is shown in its normal expanded condition. As shown in FIG. 2, the bellows is closed at its outer end and is formed with a round neck 11 at its inner end which is threaded for connection to an elongated handle 12. The handle has a passage 13 therethrough which provides a fluid flow path between the bellows and a detachable adaptor for withdrawing fluid from or supplying air to an animal. The adaptor shown in FIGS. 1 and 2 is an aspirator tube or catheter 14 having a fitting 15 for securing it to the handle by a bayonet joint including a pin 16. The tube 14 is secured to the fitting 15 on a ribbed nipple 17 as indicated in FIG. 2. The fitting 15 fits within a nipple-like metal fitting 18 in which the pin 16 is secured for engagement with the bayonet slot in the tube 14. The fitting 18 is securely mounted in the end of the handle 12 and has a hex head 19 on its outer end which may be used to hold the fitting should an adaptor become stuck.

At its end to which the bellows is attached, the handle has a flexible plastic cap 20 which is screwed onto the neck 11 when the handle is attached to the bellows. The cap 20 is secured to the handle by a cover 21 which is firmly attached to the handle and holds the cap 20 in place. The cap is screwed onto threads on the outside of the neck 11 and a flat circular metal plate 22 is threaded onto the neck and lies loosely against an annular ridge 25 on the neck adjacent the bellows. The plate is securely held between the handle and the annular ridge when the handle is tightened into position on the bellows. The plate 22 is thus held firmly against the handle and provides a stop against which the bellows is compressed to force the air out through the handle. The plate provides support for the entire end area of the bellows and assures uniform compression of the bellows and a minimum of undesired distortions.

The cap 20 is provided with a short central nozzle 23 which enters the end of the air passage 13 in the handle. The nozzle restricts the passage of air and produces a characteristic sound, resembling the sound of breathing, when the bellows is compressed and released. The nozzle 23 performs the further function of limiting the rate of expansion of the bellows when it is released from its compressed position.

Figure 3:
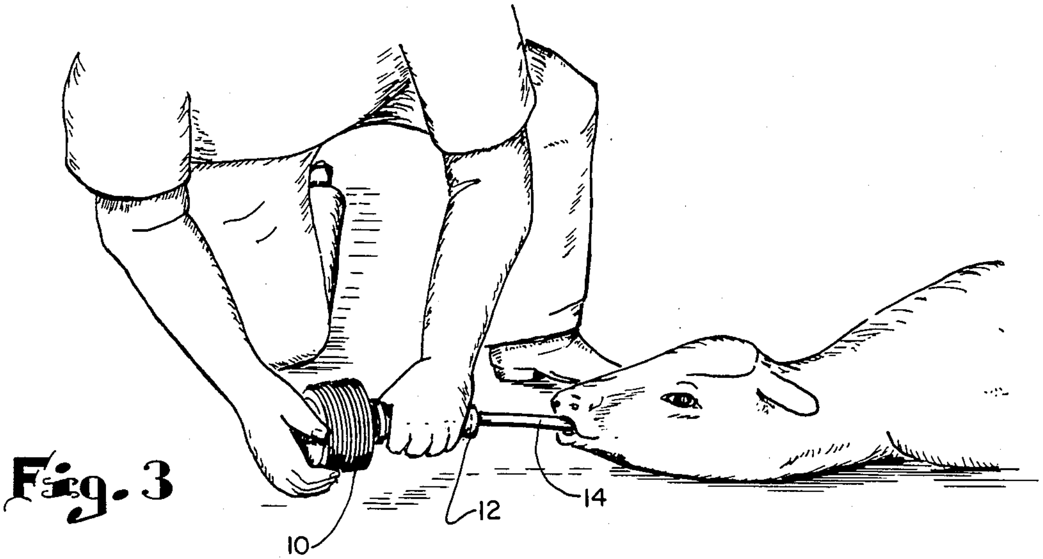
FIG. 3 is a perspective view of the device of FIG. 1 shown in use with the bellows collapsed.
Figure 4:
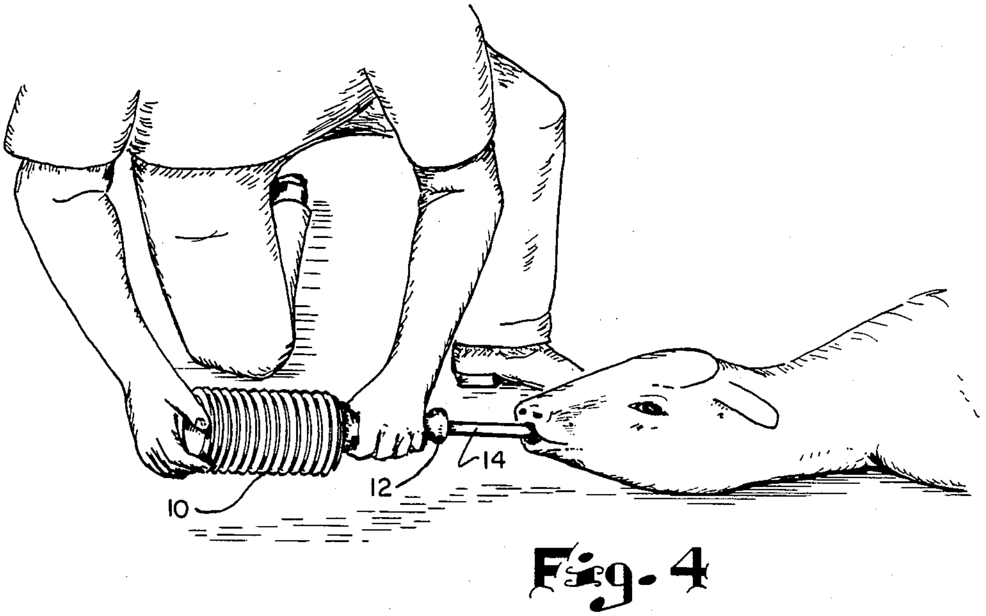
FIG. 4 is a view similar to that of FIG. 3 showing the bellows in its normal expanded state.

During the use of the aspirator of FIGS. 1 and 2, the handle is held firmly in one hand and the bellows is compressed between the hands. Then with the animal's head arched backward, the aspirator tube is inserted in the oral cavity as shown in FIG. 3 and the bellows is released carefully to drain fluid into the tube from the mouth and guttural pouch. The tube with the bellows expanded, as shown in FIG. 4, is then withdrawn and the fluid discharged.

Figure 5:
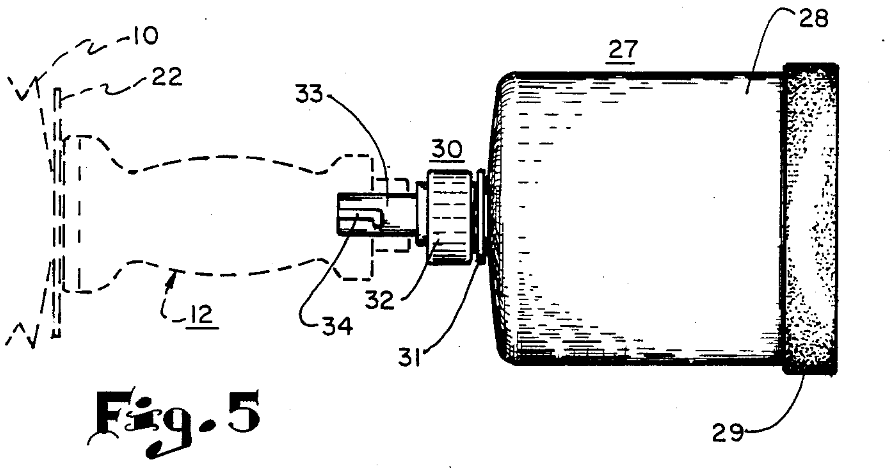
FIG. 5 is a side elevation view of a face mask for use when the device is used as resuscitator.

The nasal passages may be cleared by applying the tube to each nostril in turn and withdrawing fluid by allowing the bellows to expand. When employing the tube for aspiration, the handle 12 is held firmly by one hand and the other handle is applied so that the bellows is compressed between the hands. Then the sloping end of the tube, indicated at 26, is held against the external opening of one nostril and the bellows is allowed to expand sufficiently to withdraw mucous or other fluid from the nasal passage. This effects prompt removal of fluids from the nasal passages whereupon the tube adaptor is removed and replaced by a face mask adaptor 27 shown in FIG. 5. This adaptor comprises a hollow cylindrical body 28 which is open at its right-hand end and of a size to enclose the nose and mouth of a newborn calf or foal. The body 28 has a removable ring 29 of soft pliable plastic material about its open end; this ring is of U-shaped cross section and fits around the inside and outside walls about the rim of the cylinder 28. This ring helps to seal the face mask about the head of the animal.

The closed end of the mask is provided with a fitting 30 which is secured to a protrusion or neck 31 formed on the closed wall of the mask at the center. The fitting includes a base 32 of plastic material which is threaded on the neck 31 and may be cemented thereto. A metal nipple 33 is secured in the base 32 and has a bayonet slot 34 for engaging the pin 16 of the handling fitting 18.

Figure 6:
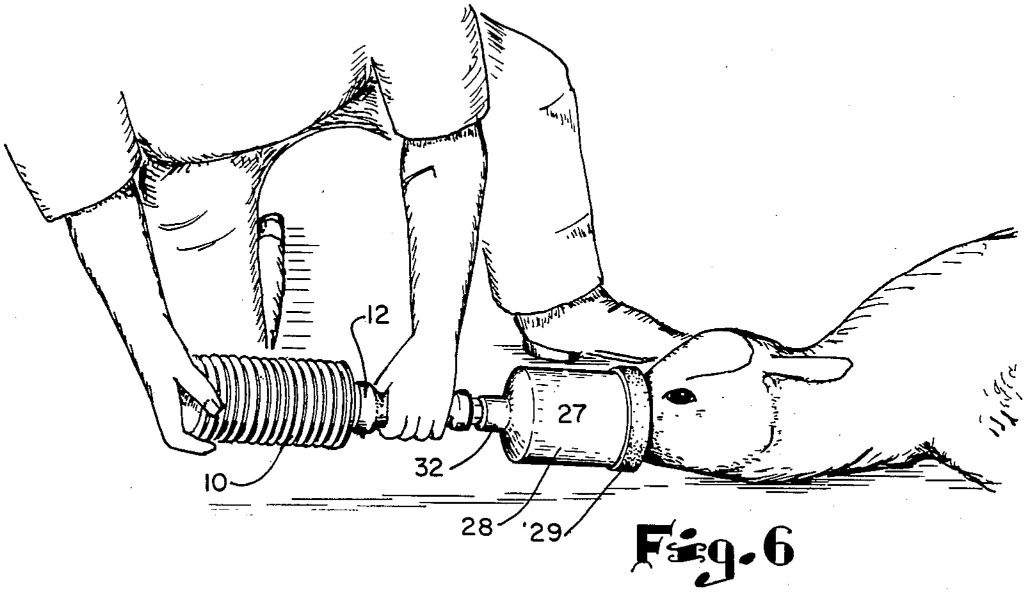
FIG. 6 is a perspective view of the apparatus in use as a resuscitator with the bellows expanded.
Figure 7:
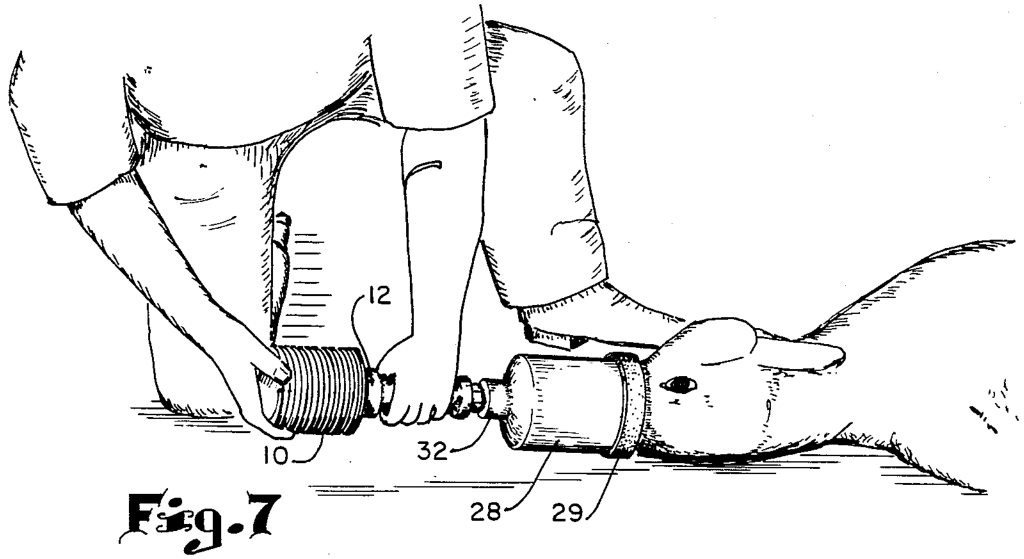
FIG. 7 is a view similar to FIG. 6 with the bellows compressed.

When the resuscitator is to be used, the animal's head is arched backward as far as possible and the mask is placed as shown in FIGS. 6 and 7. Both the nasal and oral passages of the animal are then in communication with the bellows. The bellows is then compressed from the position of FIG. 6 to that of FIG. 7, and air is thus supplied to the animal. The compression of the bellows is timed to be, say, five seconds; and the mask is then kept tight about the face for about five seconds and the bellows then is released, the seal of the mask being loosened sufficiently to permit air to enter the mask around the face and flow to the bellows through the handle 12. The release may be immediate or it may be made over a time of, say, three seconds. These steps are then repeated until the animal is breathing on its own resuscitation is terminated. When the mask is loosened to admit fresh air during expansion of the bellows, the sound produced by the nozzle 23 can be heard and provides a useful indication of the operation of the movement of air by the device.

In the event hyperventilation, which may result because of too rapid and too deep breathing, the resuscitator of this invention may be used as a rebreathing apparatus to build up carbon dioxide. This can be accomplished by fitting the mask tightly about the animal's face and observing the movement of the bellows due to the animal's breathing. When the rate of respiration has slowed, the resuscitator can be removed.

The simple and easily operated bellows and adaptor assembly provides a secure and effective arrangement for holding the device and for operating it while making sure that the adaptor is properly held in the required position on the animal. The device is easy to use and positive in operation and is very well adapted for use in the field when the facilities of the barn or yard are not available.

The whole hand grip enables the operator to hold the device securely in its required position in relation to the animal; and, at the same time, the device provides easy and positive control of the bellows held between one hand gripping the handle and the other hand holding the closed end of the bellows during compression and also during expansion when required.

Figure 8:
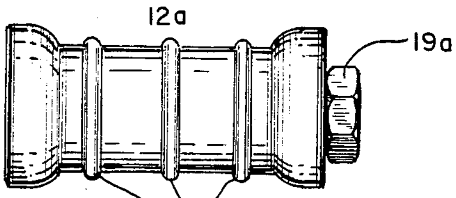
FIG. 8 is a side elevation view of a modified handle for the device.

Various configurations of the handle may be employed. By way of example, FIG. 8 illustrates a modified form of handle 12*a* which is provided with fittings like those of the handle 12 and is further provided with a plurality of spaced annular ridges 35 which help the operator to maintain the gripping position when sudden or increased forces are applied during compression of the bellows.

In the event that oxygen is desired or required during the resuscitation of an animal, a small supply tube may be introduced to the mask 28 between the face of the animal and the mask. An opening for an oxygen tube can also be drilled in the mask, say in the closed end, the tube fitting closely in the opening.

Although the invention has been described in connection with a specific embodiment, various modifications and arrangements will occur to those skilled in the art; therefore, it is not desired that the invention be limited to the details illustrated and described and it is intended by the appended claims to cover all modifications which fall within the spirit and scope of the invention.

I claim:

1. A readily portable device for effecting the aspiration and resuscitation of newborn animals which comprises:

a generally cylindrical bellows of the pleated type including means for biasing it to its expanded configuration and being longitudinally compressible to discharge air therefrom, said bellows having a pleated cylindrical side wall and a non-perforated end wall at one end and an opposite end wall having a central opening at its other end, an elongated rigid tubular fitting having an open longitudinally extending passage therethrough from end to end and with one end connected to said bellows about said opening in open communication with the interior of said bellows and affording the passage of air to and from said bellows, a detachable adaptor having an open passage extending therethrough from end to end with one end connected to the other end of said fitting in communication with said passage in said fitting and animal connection means connected to the other end of said adaptor in communication with the passage in said adaptor having a configuration for engagement with an animal for providing open communication between said bellows and a respiratory passage of the animal, said open passages in said fitting and adaptor defining a bidirectional, substantially unobstructed flow path between said bellows and said animal connection means, the external configuration of said fitting providing a whole hand grip for holding the device with said adaptor attached thereto and with said animal connection means in communication with a respiratory passage of an animal while manipulating said bellows with the other hand to deliver air to or withdraw fluid from the passage.

2. A device as set forth in claim 1 wherein said animal connection means includes a mask for providing concurrent communication with the oral and nasal passages of the animal and the connection with said fitting is of the quick detachable type.

3. A device as set forth in claim 1 wherein said fitting has an external configuration for facilitating the holding of the device against longitudinal movement during manipulation of the bellows by the other hand.

4. A device as set forth in claim 1, including means for providing a restriction in the passage between said bellows and said adaptor for producing a characteristic sound upon the passage of air therethrough and for limiting the rate of return of the bellows from its compressed to its normal expanded configuration.

5. The invention set forth in claim 1 wherein the connection between said bellows and said tubular fitting includes a neck extending from said one end of said bellows about said opening, threads on said neck and within said end of said fitting for threaded engagement, an annular ridge on said neck between said threads thereon and said end of said bellows, a circular metal plate having a central opening engageable with said threads on said neck for positioning between said threads and said annular ridge whereby said plate is securely held against said ridge when said fitting is tightened into position on said bellows and said bellows is secured in a fixed position on said neck and spaced slightly from said bellows, said plate having a diameter approximately that of said bellows and the pleats of said bellows when compressed being pressed against the outer edge of said plate and being uniformly compressed against said plate.

6. A device as set forth in claim 1 wherein said bellows, said tubular fitting and said adaptor are in alignment along a central longitudinal axis.

7. A device as set forth in claim 1 wherein said animal connection means is an aspirator tube for insertion in the oral passage of the animal and the connection with said fitting is of the quick-detachable type.

* * * * *